US010064613B2

(12) United States Patent
Davis et al.

(10) Patent No.: US 10,064,613 B2
(45) Date of Patent: Sep. 4, 2018

(54) ILLUMINATED SURGICAL RETRACTOR SYSTEM

(71) Applicants: James M. Davis, Naples, FL (US); Kim A. Marsh, Naples, FL (US)

(72) Inventors: James M. Davis, Naples, FL (US); Kim A. Marsh, Naples, FL (US)

(*) Notice: Subject to any disclaimer, the term of this patent is extended or adjusted under 35 U.S.C. 154(b) by 280 days.

(21) Appl. No.: 14/880,632

(22) Filed: Oct. 12, 2015

(65) Prior Publication Data

US 2016/0100751 A1 Apr. 14, 2016

Related U.S. Application Data

(60) Provisional application No. 62/062,329, filed on Oct. 10, 2014.

(51) Int. Cl.
| | | |
|---|---|---|
| *A61B 17/02* | (2006.01) | |
| *A61B 1/07* | (2006.01) | |
| A61B 17/00 | (2006.01) | |
| A61B 90/30 | (2016.01) | |

(52) U.S. Cl.
CPC ...... *A61B 17/02* (2013.01); *A61B 2017/0046* (2013.01); *A61B 2017/00946* (2013.01); *A61B 2090/306* (2016.02)

(58) Field of Classification Search
CPC .............. A61B 17/02; A61B 2090/306; A61B 2017/0046; A61B 2017/00946
See application file for complete search history.

(56) References Cited

U.S. PATENT DOCUMENTS

| | | | | | |
|---|---|---|---|---|---|
| 2,483,660 | A | * | 10/1949 | Morris | C03B 9/353 279/97 |
| 3,559,507 | A | * | 2/1971 | Wagner | B25B 17/02 475/270 |
| 3,881,448 | A | * | 5/1975 | Hallstrom | A01J 3/00 119/14.19 |
| 4,052,980 | A | * | 10/1977 | Grams | A61B 1/07 600/211 |
| 5,468,247 | A | * | 11/1995 | Matthai | A61F 15/02 30/339 |
| 6,322,499 | B1 | * | 11/2001 | Evans | A61B 17/00008 600/210 |
| 6,387,047 | B1 | * | 5/2002 | Duhaylongsod | A61B 17/0281 600/228 |
| 6,817,978 | B2 | * | 11/2004 | Holland | A61B 17/00008 600/210 |

(Continued)

*Primary Examiner* — Zade Coley
(74) *Attorney, Agent, or Firm* — William E. Noonan (57) ABSTRACT

An illuminated surgical retractor system includes an elongate handle having a central channel for receiving a fiberoptic cable therethrough. A trailing end of the fiberoptic cable is operatively attached to a fiberoptic illuminator. The opposite leading end of the fiberoptic cable is releasably secured to an optical coupler positioned within the channel of the handle. A retractor blade assembly releasably supports a light carrier such that an inlet of the light carrier is releasably engageable with the optical coupler and the light carrier communicates with the fiberoptic cable. The light carrier includes a light projecting portion, which conformably engages a blade of the retractor blade assembly and which projects light conducted through the light carrier to illuminate the surgical site.

20 Claims, 8 Drawing Sheets

(56) References Cited

U.S. PATENT DOCUMENTS

| | | | | |
|---|---|---|---|---|
| 2003/0139651 A1* | 7/2003 | Holland | ........... | A61B 17/00008 600/245 |
| 2003/0220547 A1* | 11/2003 | Holland | ........... | A61B 17/00008 600/245 |
| 2004/0236185 A1* | 11/2004 | Holland | ........... | A61B 17/00008 600/212 |
| 2004/0242971 A1* | 12/2004 | Holland | ........... | A61B 17/00008 600/245 |

* cited by examiner

ILLUMINATED SURGICAL RETRACTOR SYSTEM

RELATED APPLICATION

This application claims the benefit of Provisional Application Ser. No. 62/062,329 filed Oct. 10, 2014.

FIELD OF THE INVENTION

This invention relates to an illuminated retractor system for use in medical and surgical procedures. More particularly, the invention relates to a surgical retractor system featuring a universal handle and conveniently replaceable and interchangeable retractor blades and light carriers.

BACKGROUND OF THE INVENTION

Surgical retractors are commonly used by surgeons to separate the edges of a surgical incision or wound. Such instruments are also utilized to restrain the organs and tissues of a patient undergoing surgery so that body parts under the surgical incision may be more readily accessed. Most retractors employ one or more curved, hooked or angled steel blades attached to a handle that is manipulated during surgery by the surgeon or other medical personnel.

Recently, surgical retractors have been improved by the use of lighting systems that are mounted to the retractor blades. In such products, a light projecting element is typically attached to the blade and light is supplied to that element by a fiberoptic illuminator and interconnected fiberoptic cable. Such lighting systems illuminate the surgical site so that surgery is facilitated and improved surgical results are achieved.

Conventional illuminated surgical retractors exhibit various drawbacks. Most such systems are not very versatile. Different types of surgery and patients having differing physical features may require the use of various sizes and shapes of retractors for respective applications. The hospital or other surgical facility must therefore maintain a large number of differently sized and configured retractor systems, which can be quite costly. By the same token, conventional surgical retractors are typically constructed as an integrated system wherein the fiberoptic cable, handle, blade and light carrier care not practically separable or interchangeable. As a result, if a single one of these components fails, the entire retractor system must be replaced. This is not only expensive, it can also cause an inconvenient and potentially dangerous delay during a time sensitive surgical procedure.

Conventional illuminated retractors can also be awkward to manipulate and difficult to properly position and hold securely in place so that optimum surgical lighting is provided. Indeed, the need exist for a surgical lighting system that not only effectively retracts surgical incisions and restrains organs and tissues, but also better illuminates the surgical site so that improved surgical results are achieved.

SUMMARY OF THE INVENTION

It is therefore an object of the present invention to provide an illuminated surgical retractor system wherein the individual components of the retractor system, including the retractor blade and light conducting components may be quickly and conveniently interchanged and replaced as needed.

It is a further object of this invention to provide an illuminated surgical retractor system that allows various different retractor blade sizes and configurations to be used interchangeably, and quickly and conveniently replaced as required without having to change the entire retractor system.

It is a further object of this invention to provide an illuminated surgical retractor system that permits individual components of the retractor that have failed to be quickly and conveniently replaced without unduly delaying time-sensitive surgery.

It is a further object of this invention to provide an illuminated surgical retractor system that allows effectively lighted retractors to be readily manipulated and positioned so that illumination of the surgical site is optimized.

It is a further object of this invention to provide an illuminated surgical retractor system that provides for more convenient hand-held manipulation and positioning of the lighted retractor blades and which enables the lighted blades to be held in place by the use of conveniently bendable and self-sustaining fiberoptic cables.

It is a further object of this invention to provide an illuminated surgical retractor system that utilizes improved, durable lighting components that conduct and project light onto a surgical site more effectively than is accomplished by conventional devices.

It is a further object of this invention to provide an illuminated surgical retractor system that employs a universal grip that may be securely, comfortably, and effectively manipulated by a surgeon or other medical personnel during a surgical procedure.

It is a further object of this invention to provide an illuminated surgical retractor system featuring parts that remain securely interconnected during use but which may be quickly and conveniently interchanged and replaced as required.

This invention features an illuminated surgical retractor system including an elongate handle having an interior channel formed longitudinally therethrough for receiving a light conducting fiberoptic cable that is attached at a light input end to a fiberoptic illuminator. A generally tubular optical coupler is receivable within the interior channel of the handle. The optical coupler includes an elongate central bore plus inlet and outlet ports that communicate with the central bore at respective ends of the coupler. The inlet port is communicably and releasably interengaged by a leading light output end of the fiberoptic cable. The opposite outlet port of the optical coupler is releasably and communicably interengaged by a light carrier composed of a solid and preferably one-piece light conducting and projecting material. A retractor blade assembly is releasably interengaged with a receptacle formed in a leading end of the handle and in communication with the central channel of the handle. The retractor blade assembly includes a mounting collar that is received by the receptacle of the handle. The mounting collar has an interior slot for receiving the light carrier such that an inlet end of the light carrier extends from the mounting collar and is releasably interengageable with the outlet of the optical coupler within the handle. The retractor blade assembly also includes a holder section attached to and extending from a forward end of the mounting collar. The holder section defines a conduit for accommodating an intermediate light transmitting portion of the light carrier therein. A retractor blade extends from the holder section and a leading light projecting portion of the light carrier engages and is secured to the retractor blade. The system operates to transmit light from the fiberoptic illuminator, through the fiberoptic cable and to the light carrier via the optical coupler such that the light projecting portion of the light carrier projects light onto a surgical site with which the retractor blade is engaged.

In a preferred embodiment, the optical coupler has an internally threaded inlet for releasably engaging a complementary threaded leading end of the fiberoptic cable such that the fiberoptic cable is releasably attachable to the optical coupler. The inlet end of the light carrier may include an annual groove that is releasably lockable with a complementary locking component carried within the outlet port of the optical coupler. The complementary releasable locking component within the outlet of the optical coupler may include an O-ring or bearings resiliently mounted within the coupling and engageable with the annular groove of the light carrier. The annular groove preferably has a generally U-shaped cross section, which strengthens the light carrier.

The mounting collar may include a longitudinally oriented interior slot and a longitudinal opening or entry may be formed through the outer surface of the mounting collar and into the interior slot. The handle receptacle may include adjoining large and small diameter sections and the mounting collar may include complementary large and small diameter sections that fit generally conformably within the large and small diameter sections respectively of the handle receptacle when the mounting collar is received by the handle receptacle. The handle receptacle may include an annular groove for receiving one or more spring biased bearings carried by the mounting collar to releasably hold the mounting collar and thereby the retractor blade assembly and supported light carrier within the handle receptacle. In this position the retractor blade assembly and light carrier are also able to rotate within the handle. By pulling the retractor blade assembly outwardly from the handle receptacle with sufficient force, the one or more bearings are caused to resiliently retract and the retractor blade assembly can be released from the handle.

A fastening element may be operably connected to a complementary threaded hole in the handle. The longitudinal opening and interior slot in the mounting collar may be aligned with the threaded hole and the fastening element may be tightened in the threaded hole and engaged with the interior slot in the mounting collar to bear against the light carrier and lock the attached retractor assembly within the handle so that these components cannot be rotated within or removed from the handle. Alternatively, the fastening element may be threadably loosened within the handle to permit the retractor blade and attached light carrier to rotate within the handle. Loosening the fastening element also allows these components to be disengaged from the handle. The interconnection between the annular orifice of the light carrier and the O-ring or other releasable locking component in the coupler also allows the retractor blade assembly and light carrier to rotate freely within the handle when the tightening element is sufficiently loosened.

The retractor blade assembly preferably comprises a strong and rigid metallic material such as surgical steel. Typically, the blade is formed unitarily or in one piece with the intermediate holder portion, which itself may feature a curved or angled configuration. The opposite end of the intermediate holder portion is typically welded or otherwise permanently secured to the mounting collar such that the elongate conduit of the holder portion communicates with the interior slot of the mounting collar.

The fiberoptic cable may feature a segment that is bendable but that is constructed to maintain a self-sustaining shape when the cable is bent into a selected configuration. The self-sustaining segment of the fiberoptic cable may feature a gooseneck construction with a longitudinal series of metallic annular pieces that are interengaged to achieve the self-sustaining shape when the cable is bent along the self-sustaining segment.

The optical coupler may include a relatively wide central portion having a knurled outer surface that facilitates manipulation of the optical coupler and attachment of the fiberoptic cable and light carrier to respective ends thereof. The inlet and outlet ports of the optical coupler are formed in respective reduced diameter end portions of the connector component.

The handle may include a plurality of longitudinally spaced grooves or undulations that facilitate handling and manipulation of the retractor system. A trailing end of the handle may include a flange through which an entry opening is formed with the central channel for receiving the fiberoptic cable. An opposite leading end of the handle may include a cylindrical segment within which the receptacle is formed for receiving the mounting collar of the retractor blade and holder assembly.

The light carrier, which is preferably composed of a light conducting and projecting medical grade plastic, may include a curvature or angle that generally conforms to the shape of the elongate intermediate holder portion of the blade. A retainer clip may be employed to secure a distal end of the light carrier the retractor blade. The retractor blade may include a distal tip portion that extends at a downward angle from the blade. The tip portion may also include a serrated inner surface. The light projecting portion of the light carrier may be sized and configured to generally conform to the blade of the retractor blade assembly. The light projecting portion may include a frosted area for projecting and dispersing light therefrom.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
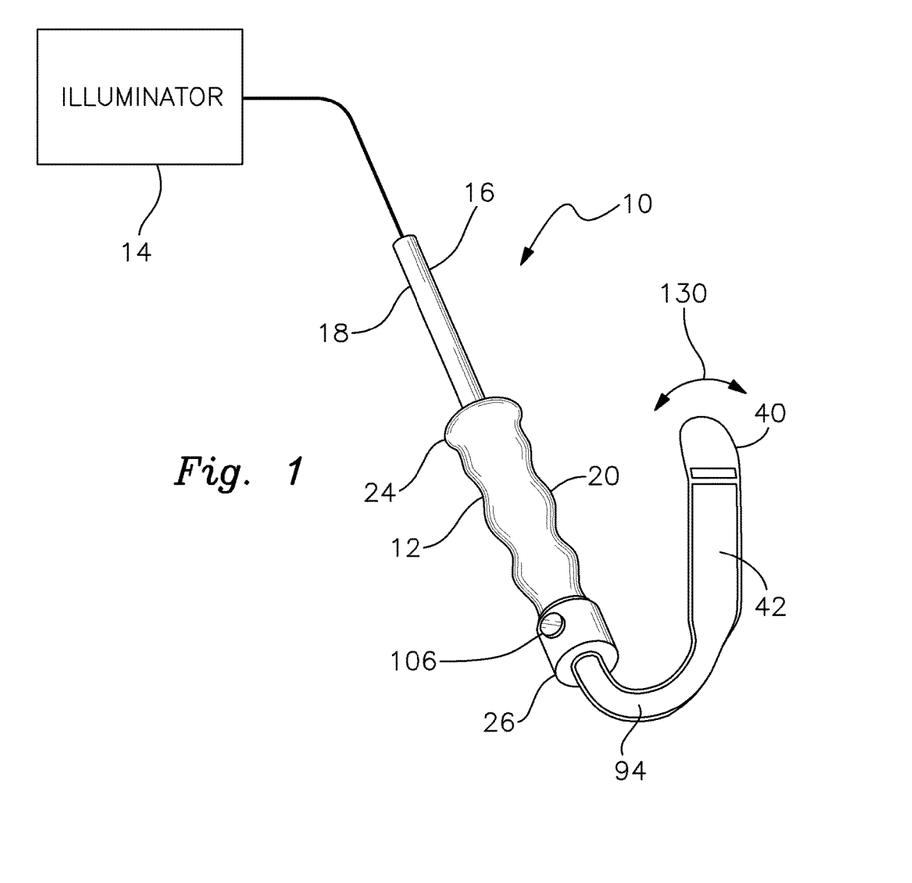
FIG. 1 is a partially perspective and partially schematic view of preferred an illuminated surgical retractor system in accordance with this invention.
Figure 2:
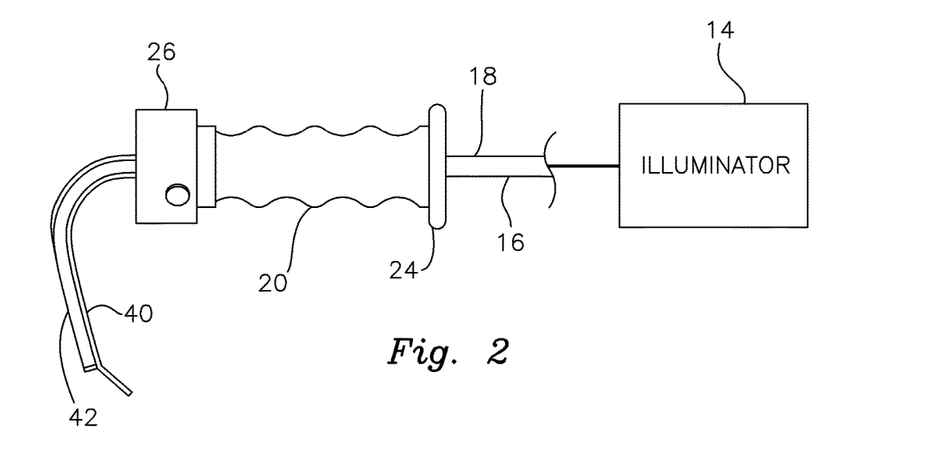
FIG. 2 is an alternative partially schematic and partially perspective view of the refractor system in an assembled condition.

There is shown in FIGS. 1 and 2 an illuminated surgical retractor system 10, which is intended for use during surgical and related medical procedures. For example, system 10 may be used effectively for various types of plastic surgery including but not limited to breast augmentation. The system is also extremely effective for use in virtually all types of thoracic surgery involving the chest or abdomen wherein the edges of a surgical incision must be separated and/or tissue, muscles and internal organs must be constrained and the surgical site illuminated. It should be understood that the specific medical and surgical applications for which system 10 may be used are not a limitation of this invention.

Illuminated retractor system 10 includes a hand-held retractor apparatus 12 that is interconnected to a standard fiberoptic illuminator 14 by a fiberoptic cable 16. Various types of fiberoptic illuminators, which are either conventional or to be developed may be employed within the scope of this invention. The light source may include, without limitation, neon, xenon and any and all various other types of light source. The fiberoptic cable includes multiple strands of optical fibers constructed in a conventional manner. Cable 16 also includes a self-sustaining jacket 18 that is constructed and provides benefits which as described more fully below.

Figure 3:
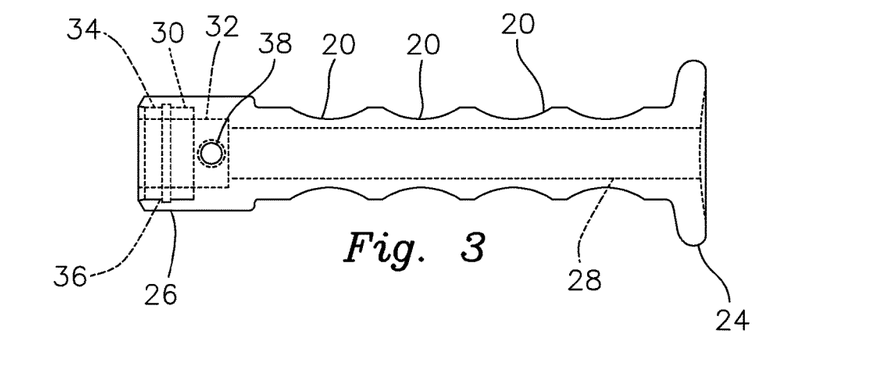
FIG. 3 is an elevational side view of the handle component by itself.

Hand-held retractor apparatus 12 features a non-slip and ergonomically shaped handle 20, which is shown alone in FIG. 3. Handle 20 is composed of a surgical grade plastic and is designed for convenient and sure handed use. The handle includes grip assisting grooves or undulations 22 formed circumferentially about the handle. A trailing end of handle 20 includes an integral flange 24 and the opposite leading end of the handle includes a cylindrical section 26. As best shown in FIG. 3, handle 20 includes an interior channel 28 that extends longitudinally through the handle from the trailing flanged end 24 to the leading cylindrical end 26. A retractor mounting receptacle 30 is formed within cylindrical portion 26 for communicating with a leading end of channel 28. Receptacle 30 is configured to accommodate other components of retractor apparatus 12 in a manner described more fully below. Specifically, receptacle 30 includes an inner small diameter section 32, an adjoining larger diameter section 34 that is open at the leading end of handle 20 and an annular groove 36 that surrounds large diameter section 34 of receptacle 30. A pair of opposing threaded holes 38 (one of which is shown in FIG. 3) are formed radially through cylindrical portion 26 of handle 20 for receiving respective locking set screws as is described below.

As further shown in FIGS. 1 and 2, retractor apparatus 12 also includes a stainless steel retractor blade assembly 40 and a light conducting and projecting carrier component 42 that is mounted to and held by blade assembly 40. As is described below, blade assembly 40 is attached to and extends from the leading cylindrical end 26 of handle 20. Light carrier 42 is supported by the blade such that it is communicably connected to the light conducting optical fibers of fiberoptic cable 16 within channel 28 of handle 20.

Figure 4A:
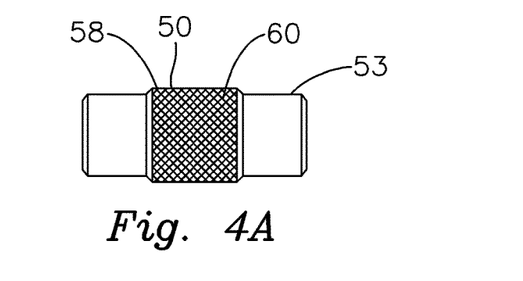
FIG. 4A is an elevational side view of the optical coupler for operably joining the fiberoptic cable to the light carrier.
Figure 4B:
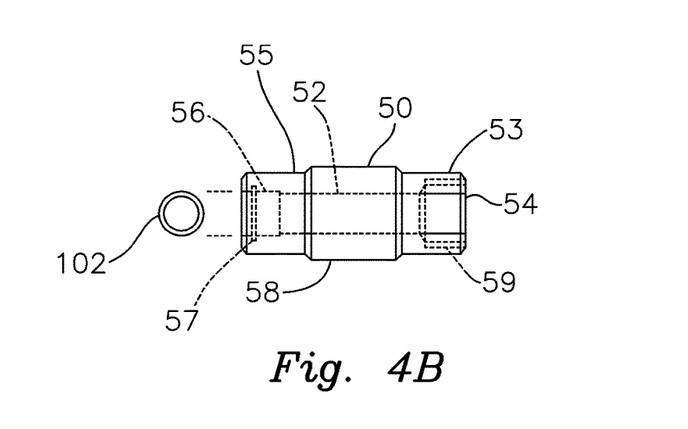
FIG. 4B is a side elevational view of the optical coupler and, more particularly, depicting the inlet, outlet and central bore extending therethrough.

FIGS. 4A and 4B depict an elongate optical coupler 50 which communicably interconnects light carrier 42 to the leading end of fiberoptic cable 16 within handle 20. Optical coupler 50 includes a central bore 52 with an inlet 54 and outlet 56 formed at respective ends of the bore within reduced diameter cylindrical sections 53 and 55 respectively. An annular groove 57 surrounds outlet 56 for receiving an O-ring that functions in the manner described below. The coupler further includes a relatively large diameter central cylindrical section 58 that has a knurled outer surface 60. Bore 52 extends through the axially aligned cylindrical sections 53, 55 and 58.

Inlet 54 of coupler 50 is attached by threads 59 to the threads (not shown) conventionally formed at the leading end of fiberoptic cable 16. As a result, when the illuminator 14 is activated and light is transmitted through fiberoptic cable 16, that light is transmitted from the attached leading end of the cable through central bore 52 of optical coupling 50 and discharged through outlet 56 of coupler 50. This is again described more fully in conjunction with the operation of the system which follows. The optical coupler itself is received within interior channel 28 of handle 20 such that the coupler is movable longitudinally through the handle. Nonetheless, the knurled surface 50 of central section 50 constrains such longitudinal movement of the optical coupler within the handle somewhat by frictionally engaging the interior surface of the handle channel 28. Typically, the coupler is moved longitudinally through the handle by pushing and pulling the optical cable through the handle as required.

Figure 5:
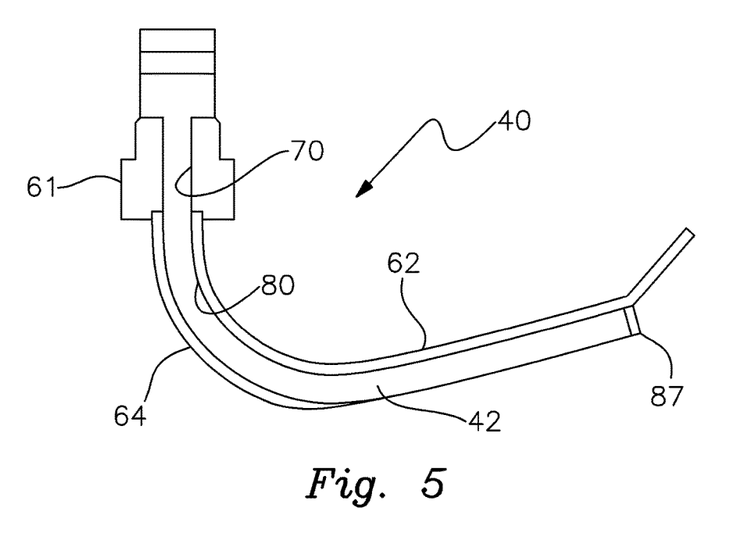
FIG. 5 is a perspective view of the light conducting and projecting carrier installed in the retractor blade assembly.
Figure 6A:
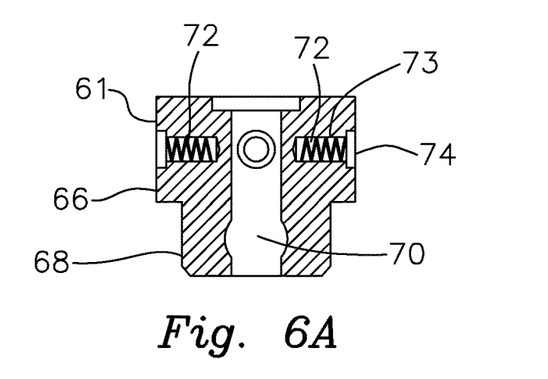
FIG. 6A is a cross sectional view of the mounting collar of the holder.
Figure 6B:
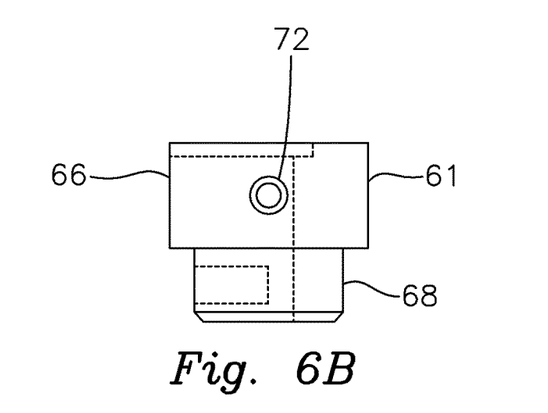
FIG. 6B is a side elevational view of the mounting collar oriented at 90 degrees to the view of FIG. 6A.
Figure 6C:
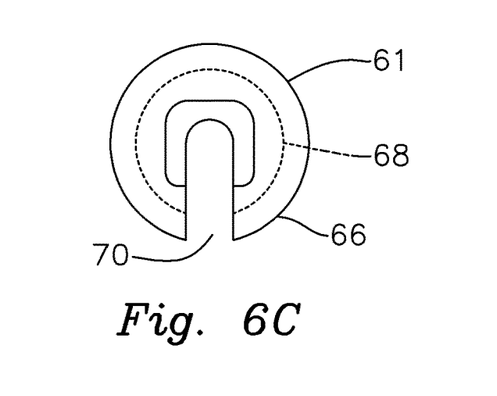
FIG. 6C is an end view of the mounting collar.

FIG. 5 depicts the light supportive retractor blade assembly 40 operatively engaged with light carrier 42. In particular, assembly 40 includes a mounting collar 61, a substantially flat blade 62 and a curved and slotted intermediate holder section 64 that interconnects collar 61 and blade 62. Collar 61, shown alone in FIGS. 6A-6C, features unitarily interconnected large and small diameter sections 66 and 68, respectively. A slot 70 extends longitudinally through mounting collar 61 for receiving a short segment of light carrier 42 that has a corresponding cross sectional shape. An aligned entry or opening into slot 70 is formed through the outer surface of collar 61. As best shown in FIGS. 6A and 6B, collar 61 also includes a pair of opposing compartments 72 for accommodating respective locking springs 73 and bearings 74 that are urged outwardly from large diameter section 66 of collar 61 as best shown in FIG. 5.

Figure 7A:
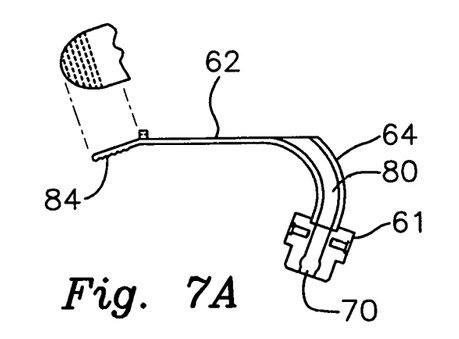
FIG. 7A is an elevational, cross sectional view of the retractor assembly by itself.
Figure 7B:
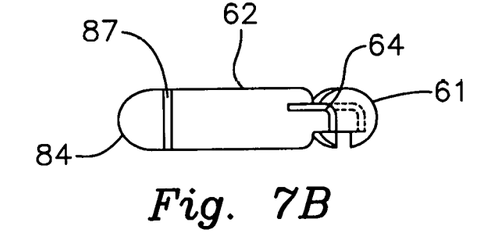
FIG. 7B is a top plan view of the retractor assembly.

FIGS. 7A and 7B show retractor blade 62 interconnected to mounting collar 61 by curved and slotted intermediate holder section 64. The substantially flat blade 62 is unitarily connected to holder section 64. The intermediate holder section is, in turn, welded or otherwise permanently secured to collar 61 such that a longitudinal conduit 80 of intermediate holder section 64 is substantially aligned and communicates with longitudinal slot 70 in collar 61. This allows the curved light carrier 42 to be easily and snugly received by the aligned slot 70 and conduit 80 formed in collar 61 and intermediate holder section 64 respectively. See FIG. 5. It should be understood that retractor blade assembly 40, in particular, blade 62 and intermediate holder section 64 may have alternate shapes, sizes and curvatures within the scope of this invention to address various surgical, illumination and/or patient needs or concerns.

Figure 7C:
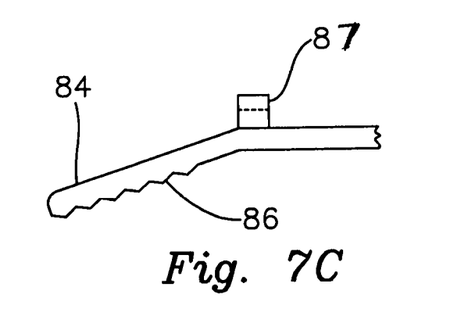
FIG. 7C is a side elevational view depicting the distal end of the blade.
Figure 8A:
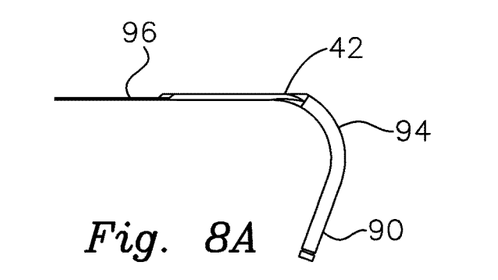
FIG. 8A is a side elevational view of the light carrier shown by itself.
Figure 8B:
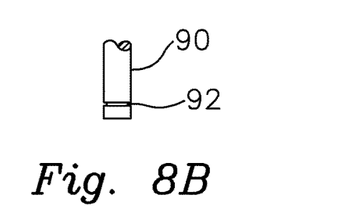
FIG. 8B is an enlarged fragmentary view of the inlet portion of the light carrier and particularly depicting the annular groove formed in the light carrier for retaining the light carrier within the outlet port of the optical coupler.
Figure 8C:
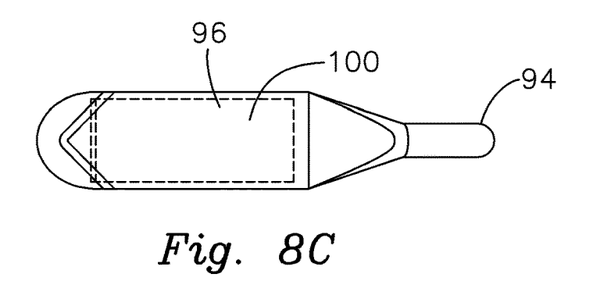
FIG. 8C is a top plan view of the light carrier.
Figure 8D:
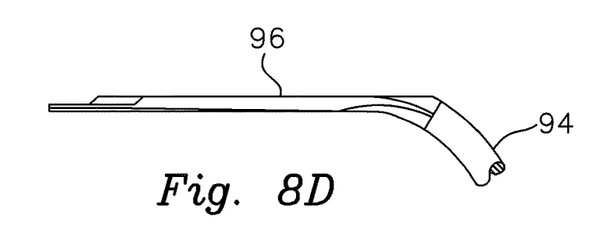
FIG. 8D is an enlarged side elevational view of the distal end of the light carrier more particularly depicting a substantially flat light projecting portion of the light carrier.
Figure 8E:
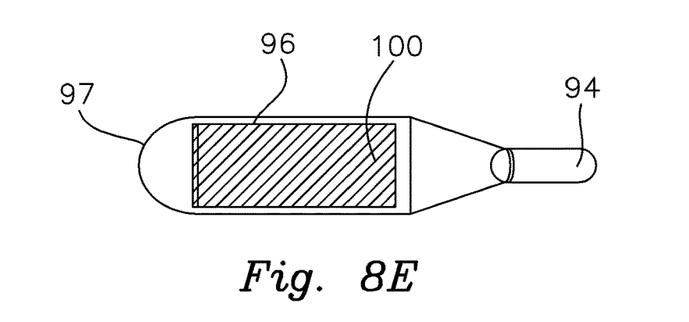
FIG. 8E is a top plan view of the light carrier, which particularly illustrates the frosted coating formed on the light carrier for projecting and dispersing light therefrom.

As further shown in FIG. 7A-7C, a distal tip section 84 of retractor blade assembly 40 is unitarily connected to blade 62 and extends from blade 62 at an acute angle, as best shown in FIGS. 7A and 7C. Tip 84 includes an inner serrated surface 86 that provides for improved frictional engagement and gripping of the edges of incisions and bodily parts. As a result, the retractor blade securely grips a part of the body to be retracted. The incision, tissue or organ is thereby more effectively held securely in place and out of the surgeon's way during the surgical procedure.

A light carrier retaining clip 87 is attached to a top surface of blade 62 proximate the junction with angled tip 84. Clip 87 secures a distal end of the supported light carrier to blade 62 as is described more fully below.

FIGS. 8A-8E further disclose the light carrier by itself. The light carrier includes a light inlet end section 90, FIGS. 8A and 8B, that has a cylindrical, rod-like shape with an annular groove 92 formed circumferentially about end section 90. See also FIG. 5. Annular groove 92 employs a generally U-shaped cross sectional configuration which is much stronger and therefore supports the light carrier much more securely than a V-shaped cross sectional configuration. The inlet end section 90 of light carrier 42 extends rearwardly from the reduced diameter section 68 of collar 61 in the manner shown in FIG. 5. Inlet end 90 of light carrier 42 is received within outlet 56 of optical coupler 50 shown in FIG. 4B. An O-ring 102 received within annular groove 57 of coupler 50 snugly interengages annular groove 92 of light inlet end section 90 such that the light carrier is releasably interengageable with and attachable to the outlet of coupler 50.

Light carrier 42 also includes a curved or angled rod-like intermediate section 94, which unitarily and communicably connects inlet section 90 with a generally flat light projecting section 96. Carrier 42 typically comprises a light conductive plastic material as disclosed in U.S. Pat. Nos. 5,931,670, 6,059,723, 6,304,712, and 6,176,824 (the specifications of which are hereby incorporated by reference), which material both effectively transmits light and projects the transmitted light from exterior surfaces thereof. More particularly, the outer surface of light projecting portion 96 includes a frosted surface 100 that disperses and brightly projects white light from carrier 42. Light projecting portion 96 is generally conformably engaged with and attached to blade 62 of assembly 40. Specifically, clip 87 extends across and holds a distal end of the light projecting section of light carrier 42. It should be understood that the light carrier components may have various different sizes and shapes to generally conform with the size and shape of the retractor blade assembly to which the light carrier 42 is mounted.

An important feature of this invention is that various selected sizes and shapes of retractor blade assemblies 40, light carriers 42 and optical coupling components 50 may be employed with the same universal handle 20, cable 16 and fiberoptic illuminator 14. Indeed, the individual components may be interchanged for different patients and surgical procedures and replaced as required during or prior to a surgical procedure. These benefits are described more fully below.

Illuminator system 10 may be assembled in the following manner. Fiberoptic cable 16 is interconnected at a first end to illuminator 14. The opposite, output end of cable 16 is inserted through interior channel 28 of handle 20 such that the discharge end of the fiberoptic cable extends beyond the receptacle 34 in the leading end of the handle. Optical coupler 50 is then attached to the fiberoptic cable by threadably interengaging threaded inlet 54 of coupler 50 with the threaded outlet at the discharge end of the cable. Optical coupler 50 with fiberoptic cable 16 operatively attached thereto thus extends through and beyond the leading cylindrical end 26 of handle 20. See FIG. 9. A locking screw 106 operatively received in previously described hole 38 of handle 20 is loosened so that the fiberoptic cable 16 and attached optical coupler 50 are freely movable longitudinally through the central channel 28 of handle 20. The retractor assembly 40 and light carrier 42 are then selected to meet the needs of a particular surgical procedure, patient size or other varying parameter involved in a particular surgery. Typically, the selected light carrier is attached to blade assembly 40 by inserting the inlet end section 90 of the carrier through the longitudinal slot 70 of collar 61 and likewise fitting angled portion 94 of carrier 42 into curved slot 80 formed in the intermediate holder section 64 of blade assembly 40. See FIG. 5. The flat portion 96 of carrier 42 is substantially flush with the upper surface of blade 62 and the distal tip 97 of carrier 62 fits under and is secured in place by retaining clip 87 of retractor blade assembly 40.

Figure 9:
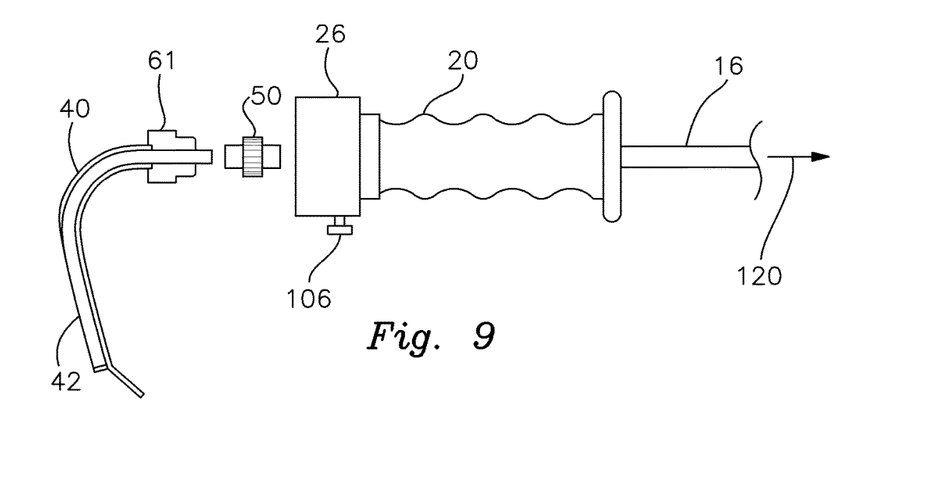
FIG. 9 is a perspective view of the retractor blade assembly and attached light carrier prior to attachment of the light carrier to the optical coupler, which is depicted extending forwardly of the handle and attached to the leading end of the fiberoptic cable.

The assembled retractor blade assembly 40 and light carrier 42 are attached to the distal end of optical coupler 50 in the manner shown in FIG. 9. Specifically, the inlet end section 90 of light carrier 42 is inserted into outlet 56 of optical coupler 50, FIG. 4B. The inlet end of the light carrier is pushed into the outlet 56 of coupler 50 until the O-ring 102 carried in annular groove 57 is snap fit into the annular groove 92 formed in inlet end 90 of light carrier 42. This attaches light carrier 42 and retractor blade assembly 40 securely, but releasably to optical coupler 50. The interconnected components can later be released by simply exerting sufficient force to separate and pull apart the light carrier and retractor assembly from the coupler. Such separation is typically performed when changing or replacing the light carrier and retractor blade assembly.

To complete assembly of system 10, the fiberoptic cable is drawn longitudinally through the interior channel of the handle as indicated by arrow 120 in FIG. 9. This pulls the optical coupler 50 into channel 28 and likewise pulls collar 61 of retractor blade assembly 40 into receptacle 34 formed in the leading cylindrical end of handle 20. More particularly, reduced diameter cylindrical section 68 of collar 61 fits into reduced diameter section 32 of receptacle 30; large diameter section 66 of collar 61 likewise fits into large diameter section 34 of receptacle 30. The spring biased bearings 74 carried by collar 61 snap fit into annular groove 36 formed about receptacle 30 of handle 20. This interconnection securely, but releasably attaches the retractor blade assembly 40 and supported light carrier 42 to the leading end of handle assembly 20. See FIGS. 1 and 2. The interconnection between spring biased bearings 74 and the interior annular groove 36 of handle 20 also allows the retractor blade assembly and supported light carrier to rotate freely relative to the handle as indicated by double headed arrow 130 in FIG. 1. This enables the retractor blade and light carrier to be quickly and conveniently maneuvered and oriented into a desired position during the surgical procedure, which permits both effective lighting and effective retraction during the surgical procedure.

When assembly is complete, system 10 is utilized to perform illuminated surgical retraction. The flat, light projecting section 96 of light carrier 42 effectively projects light downwardly from system 10 to brightly illuminate the surgical site. The frosted area 100 is especially effective in dispersing/scattering the light so that improved surgical lighting is achieved.

Alternatively, the retractor blade assembly 40 and supported light carrier 42 may be locked in place to restrict rotation of those components within the handle. This is quickly and conveniently accomplished by aligning the longitudinal slot 70 of collar 61 with the locking/set screw 106 mounted to cylindrical end 26 of handle 20. Tightening screw 106 so that it extends through slot 70 and bears against light carrier 42 effectively locks the entire retractor blade assembly and supported light carrier in place so that they are held in a fixed position and do not unintentionally separate from the handle during the surgical procedure. If needed, these components can always be rotated by simply loosening the set screw to permit turning of the retractor blade assembly 40 and light carrier 42 within handle 20. Loosening screw 106 also allows removal and replacement of the retractor blade assembly and attached light carrier if required.

Figure 10:
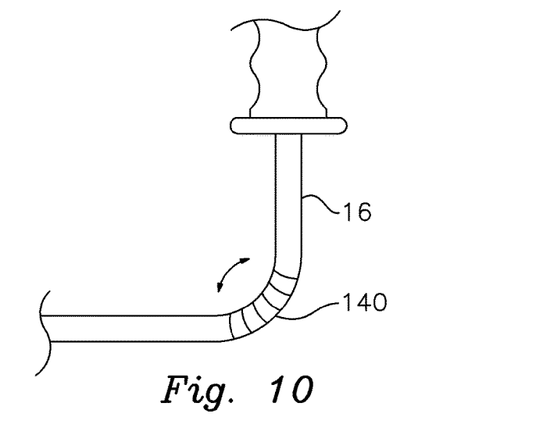
FIG. 10 is an elevational side view of the fiberoptic cable employing a bendable gooseneck section for holding the cable in a self-sustaining shape during use of the illuminated surgical retractor system.

As shown in FIG. 10, fiberoptic cable 16 may be provided with a cable jacket or sheath that features a series of segmented metallic sections 140 that resemble and are constructed analogously to the sections of a gooseneck lamp. This permits the cable to be bent and repositioned to hold a self-sustaining shape during the surgery. This can help to position and orient the cable and the illuminated surgical retractor system so that a selected position is maintained and extraneous operator manipulation and prolonged holding of the device in an awkward and tiring position are avoided.

The system of the present invention successfully allows many different sizes of retractor blades and illuminating light carriers to be interchanged and replaced as needed or desired in connection with different surgical procedures and patient requirements. In contrast to the prior art, if a single component of this system fails, the entire system does not have to be replaced. Only the defective component must be changed and needed repair or replacement can be performed quickly and conveniently. In addition, the hospital or other surgical facility does not have to maintain an unnecessarily large supply of expensive and possibly duplicate parts. Standard fiberoptic cables may be employed much more efficiently in connection with a number of variously sized retractor blades and light conducting/projecting carriers. By the same token, a single universal handle can be used with numerous combinations of retractor blades and illuminating light carriers. Medical and surgical costs are thereby reduced and much more efficient management of surgical supplies is achieved.

As previously indicated the retractor blade assembly and light carrier may have various different sizes, configurations and angles. Although generally flat blade-like shapes are depicted herein, in other embodiments, the retractor blades and light projection portion of the light carrier may feature round or alternatively configured shapes.

Accordingly, the present invention relates to an improved, highly efficient illuminated surgical retractor system. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. An illuminated surgical retractor system for use in combination with a fiberoptic illuminator and light conducting fiberoptic cable attached at a light input end thereof to the fiberoptic illuminator, said system comprising:
   an elongate handle having a longitudinal channel formed therethrough for receiving the light conducting fiberoptic cable;
   an optical coupler receivable within said channel, said optical coupler having female inlet and outlet ports and an interior bore that communicably interconnects said inlet and outlet ports, said female inlet port for receiving and being communicably and releasably interengaged by a light output end of the fiberoptic cable;
   a retractor blade assembly releasably interengaged with a receptacle formed in a leading end of said handle, said receptacle communicating with said channel formed through said handle; and
   a light carrier for attaching to said retractor blade assembly, said light carrier including a light inlet section that is received by and communicably and releasably interengaged with said female outlet port of said optical coupler and a light projecting portion communicably connected to said light inlet section, the fiberoptic illuminator being operable to transmit light through the fiberoptic cable and through said optical coupler to said light inlet section of said light carrier such that said light projecting portion of said light carrier projects light onto a surgical site with which said retractor blade assembly is engaged; said longitudinal channel formed through said handle being configured such that when said retractor blade assembly is released from interengagement with said receptacle and said light inlet section of said light carrier is disengaged from said female outlet port of said optical coupler, the fiberoptic cable and said optical coupler interengaged with the cable are selectively movable longitudinally through said channel and said receptacle to extend said optical coupler beyond said receptacle and said leading end of said handle.

2. The system of claim 1 in which said retractor blade assembly includes a mounting collar for being removably received by said receptacle of said handle and a retractor blade attached to said mounting collar, said mounting collar having a longitudinal interior slot with an aligned entry into said slot being formed longitudinally in an outer side surface of said collar for receiving said light carrier such that said light inlet section is held for releasable interengagement with said female outlet port of said optical coupler and wherein said aligned entry into said longitudinal interior slot is covered by said handle.

3. The system of claim 2 in which said retractor blade assembly further includes an intermediate holder section that interconnects said mounting collar and said retractor blade, said intermediate holder section having a conduit that is alignable with said longitudinal interior slot of said mounting collar for accommodating an intermediate light transmitting portion of said light carrier therein, which intermediate light transmitting portion of said light carrier communicably interconnects said light inlet section and said light projecting portion of said light carrier.

4. The system of claim 3 in which said intermediate holder section unitarily interconnects said mounting collar and said retractor blade of said retractor blade assembly.

5. The system of claim 3 in which said light carrier is configured to conform to the shape of said intermediate holder section and said retractor blade of said retractor blade assembly.

6. The system of claim 2 in which said handle includes a fastening hole formed therethrough into said receptacle, said mounting collar being axially rotatably adjustable in said receptacle to selectively align said entry of said longitudinal interior slot with said fastening hole and further including a fastening element that is selectively interengaged with said fastening hole and said longitudinal interior slot in said mounting collar to engage said light carrier and selectively lock said retractor assembly within said handle.

7. The system of claim 2 in which said leading end of said handle includes a cylindrical segment in which said receptacle is formed for receiving said mounting collar.

8. The system of claim 1 in which said light inlet section of said light carrier includes an annular groove that is releasably lockable with a complementary locking component carried within said outlet port of the optical coupler.

9. The system of claim 8 in which said annular groove has a U-shaped cross sectional configuration for strengthening interengagement between said light carrier and said complementary locking component.

10. The system of claim 1 in which said receptacle in said handle includes adjoining relatively large and small diameter interior cylindrical sections and said mounting collar includes complementary relatively large and small diameter exterior cylindrical sections that fit generally conformably within said relatively large and small diameter interior cylindrical sections respectively of said receptacle when said mounting collar is received by said receptacle.

11. The system of claim 1 in which said receptacle in said handle includes an annular groove for receiving one or more spring biased bearings carried by said mounting collar to releasably hold said mounting collar and thereby said retractor blade assembly and supported light carrier within said handle receptacle.

12. The system of claim 1 in which said female inlet and outlet ports of said optical coupler are formed in respective reduced diameter end portions of said optical coupler.

13. The system of claim 1 in which said light projecting portion includes a frosted area for dispersing and projecting light therefrom.

14. The system of claim 1 in which said handle includes an integral flange that fully surrounds said trailing end of said handle.

15. The system of claim 1 in which said handle includes a series of undulations arranged longitudinally along said handle to assist gripping of said handle.

16. The system of claim 1 in which said handle consists of a single unitary piece of surgical grade plastic.

17. An illuminated surgical retractor system for use with a fiberoptic illuminator, said system comprising:
- a light conducting fiberoptic cable that is attachable at a light input end thereof to the fiberoptic illuminator, said fiberoptic cable having an opposite light output end for discharging illumination produced by the fiberoptic illuminator therefrom;
- an elongate handle having a channel formed longitudinally therethrough for receiving said light output end of said light conducting fiberoptic cable and permitting said fiberoptic cable to move longitudinally through said channel to selectively maintain said light output end of said cable at a position proximate a leading end of said handle;
- a light carrier composed of a light conducting and projecting material; and
- a retractor blade assembly releasably interengaged with a receptacle formed in a said leading end of said handle and in communication with said channel of said handle, said retractor blade assembly including a mounting collar received by said receptacle of said handle, said mounting collar having an interior slot for removably receiving said light carrier such that a light inlet end of said light carrier extends from said mounting collar and is releasably interengageable and optically communicable with said light output end of said fiberoptic cable within said handle; said retractor blade assembly also including a retractor blade and a holder section interconnecting said mounting collar and said retractor blade, said holder section having a conduit for accommodating an intermediate light transmitting portion of said light carrier therein; and a light projecting portion of said light carrier engaging and being secured to said retractor blade; whereby the fiberoptic illuminator is operable to transmit light through said fiberoptic cable and to said light carrier such that said light projecting portion of said light carrier projects light onto a surgical site with which said retractor blade is engaged, said channel being configured such that when said retractor blade is released from interengagement with said receptacle and said light inlet end of said light carrier is released from interengagement with said light output end of said fiberoptic cable, said fiberoptic cable is freely movable longitudinally through said channel and said receptacle to selectively extend said light output end of said fiberoptic cable beyond said receptacle and said leading end of said handle.

18. The system of claim 17 in which said fiberoptic cable is bendable and has a self-sustaining shape.

19. The system of claim 17 in which said channel is configured to allow said fiberoptic cable to rotate axially within said channel independently of said handle.

20. An illuminated surgical retractor system for use with a fiberoptic illuminator, said system comprising:
- a light conducting fiberoptic cable that is attachable at a light input end to the fiberoptic illuminator;
- an elongate handle having a channel formed longitudinally therethrough and extending from a trailing end to a leading end of said handle for receiving a light output end of said fiberoptic cable and permitting said fiberoptic cable to selectively move longitudinally through said channel such that said light output end of said fiberoptic cable maintains a position proximate said leading end of said handle;
- an optical coupler receivable within said channel, said optical coupler having inlet and outlet ports and an interior bore that communicably interconnects said inlet and outlet ports, said inlet port for being communicably and releasably interengaged by said light output end of said fiberoptic cable;
- a retractor blade assembly releasably interengaged with a receptacle formed in said leading end of said handle, said receptacle communicating with said channel formed through said handle;
- a light carrier for attaching to said retractor blade assembly, said light carrier including a light inlet section that is communicably and releasably interengageable with said outlet port of said optical coupler and a light projecting portion communicably connected to said light inlet section, the fiberoptic illuminator being operable to transmit light through the fiberoptic cable and through said optical coupler to said light inlet section of said light carrier such that said light projecting portion of said light carrier projects light onto a surgical site with which said retractor blade assembly is engaged; and said channel being configured such that said fiberoptic cable and said interengaged optical coupler are axially rotatable within said channel and, when said retractor blade assembly is released from interengagement with said receptacle and said light inlet section of said light carrier is released from interengagement with said outlet port of said optical coupler, said fiberoptic cable and said interengaged optical coupler are selectively movable longitudinally fully through said channel and said receptacle to extend said optical coupler beyond said receptacle and said leading end of said handle.

* * * * *